(12) United States Patent
Wang et al.

(10) Patent No.: US 10,533,948 B2
(45) Date of Patent: *Jan. 14, 2020

(54) CARRIER FOR USE IN SINGLE MOLECULE DETECTION

(71) Applicants: Tsinghua University, Beijing (CN); HON HAI PRECISION INDUSTRY CO., LTD., New Taipei (TW)

(72) Inventors: Ying-Cheng Wang, Beijing (CN); Yuan-Hao Jin, Beijing (CN); Qun-Qing Li, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/119,607

(22) Filed: Aug. 31, 2018

(65) Prior Publication Data
US 2019/0079017 A1    Mar. 14, 2019

(30) Foreign Application Priority Data

Sep. 8, 2017 (CN) .......................... 2017 1 0807473

(51) Int. Cl.
*G01J 3/44* (2006.01)
*G01N 21/65* (2006.01)
*B01L 3/00* (2006.01)

(52) U.S. Cl.
CPC .......... *G01N 21/658* (2013.01); *B01L 3/5085* (2013.01); *B01L 2300/06* (2013.01); *B01L 2300/0829* (2013.01); *B01L 2300/12* (2013.01); *G01N 2021/651* (2013.01)

(58) Field of Classification Search
CPC ................. G01N 21/65; G01N 21/658; G01N 2021/656; G01J 3/02; G01J 3/44
USPC .......................... 356/244, 301; 977/773, 755
See application file for complete search history.

(56) References Cited

U.S. PATENT DOCUMENTS

| 10,132,756 B2* | 11/2018 | Jin ........................ C01B 32/158 |
| 10,145,797 B2* | 12/2018 | Jin ........................ G01N 21/65 |
| 10,330,601 B2* | 6/2019 | Wang ................... G01N 21/658 |
| 2012/0170032 A1* | 7/2012 | Zhu ..................... G01N 21/658 356/301 |
| 2015/0212003 A1 | 7/2015 | Shibayama et al. |
| 2015/0233832 A1* | 8/2015 | Maruyama .......... G01N 21/658 356/244 |
| 2015/0233833 A1 | 8/2015 | Shibayama et al. |

(Continued)

FOREIGN PATENT DOCUMENTS

| CN | 104508464 | 4/2015 |
| CN | 103575720 B | 11/2015 |

(Continued)

*Primary Examiner* — Hoa Q Pham
(74) *Attorney, Agent, or Firm* — ScienBiziP, P.C.

(57) ABSTRACT

A carrier for use in single molecule detection is related. The carrier includes a substrate; a middle layer, on the substrate; and a metal layer, on the middle layer; wherein the substrate is a flexible substrate, the middle layer includes a base and a patterned bulge on the base, the patterned bulge includes a plurality of strip-shaped bulges, the metal layer is on the patterned bulge, the carrier further includes a carbon nanotube composite structure between the metal layer and the patterned bulge.

17 Claims, 21 Drawing Sheets

(56) References Cited

U.S. PATENT DOCUMENTS

| | | | |
|---|---|---|---|
| 2016/0340233 A1 | 11/2016 | Jin et al. | |
| 2018/0003639 A1 | 1/2018 | Jin et al. | |
| 2019/0079015 A1* | 3/2019 | Wang | G01N 21/658 |
| 2019/0113461 A1* | 4/2019 | Wang | G01N 21/658 |
| 2019/0113462 A1* | 4/2019 | Wang | G01N 21/658 |
| 2019/0212475 A1* | 7/2019 | Jin | B60S 1/026 |
| 2019/0212476 A1* | 7/2019 | Jin | B60S 1/026 |
| 2019/0227198 A1* | 7/2019 | Jin | G02B 1/18 |

FOREIGN PATENT DOCUMENTS

| | | |
|---|---|---|
| CN | 105784669 A | 7/2016 |
| CN | 106276778 | 1/2017 |
| CN | 205896896 | 1/2017 |
| CN | 205898686 | 1/2017 |
| CN | 107014799 A | 8/2017 |
| TW | 201411116 | 3/2014 |

\* cited by examiner

CARRIER FOR USE IN SINGLE MOLECULE DETECTION

CROSS-REFERENCE TO RELATED APPLICATIONS

This application is related to co-pending applications entitled, "CARRIER FOR USE IN SINGLE MOLECULE DETECTION", U.S. patent application Ser. No. 16/122,976, concurrently filed on Sep. 6, 2018, "METHOD OF MAKING A CARRIER FOR MOLECULAR DETECTION", U.S. patent application Ser. No. 16/119,663, concurrently filed on Sep. 6, 2018, "METHOD FOR DETECTION MOLECULAR", U.S. patent application Ser. No. 16/119,679, concurrently filed on Sep. 6, 2018, and "MOLECULAR DETECTION DEVICE", U.S. patent application Ser. No. 16/124,496, concurrently filed on Sep. 6, 2018.

FIELD

The subject matter herein generally relates to a carrier for use in single molecule detection.

BACKGROUND

Raman spectroscopy is widely used for use in single molecule detection.

A method for detecting single molecules using Raman spectroscopy is provided. An aggregated silver particle film is coated on a surface of a glass substrate. A number of single molecule samples are disposed on the aggregated silver particle film. A laser irradiation is supplied to the single molecule samples by a Raman detection system to cause a Raman scattering and produce a Raman spectroscopy. The Raman spectroscopy is received by a sensor and analyzed by a computer. However, the substrate for carrying single molecules is usually rigid and made of rigid materials such as glass, silicon, silicon dioxide, silicon nitride, quartz, gallium nitride, alumina or magnesium oxide. Thus, the single molecules have to be extracted before the detecting from the object and the object with anomalistic shapes cannot be detected in real time, in situ, on line, or in vivo.

Therefore, there is room for improvement within the art.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views. Implementations of the present technology will be described, by way of example only, with reference to the attached figures.

DETAILED DESCRIPTION

Figure 1:
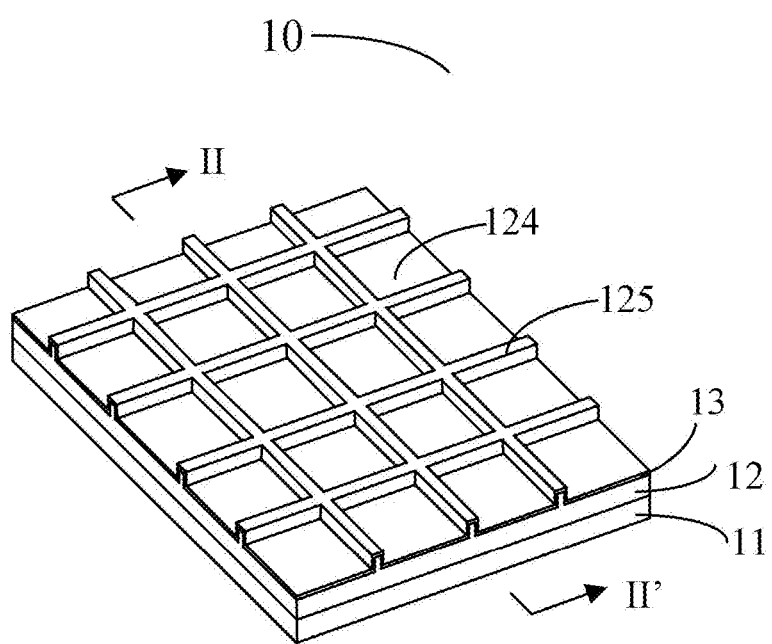
FIG. 1 is a schematic view of a carrier for use in single molecule detection.

It will be appreciated that for simplicity and clarity of illustration, where appropriate, reference numerals have been repeated among the different figures to indicate corresponding or analogous elements. In addition, numerous specific details are set forth to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale, and the proportions of certain parts may be exaggerated to better illustrate details and features. The description is not to be considered as limiting the scope of the embodiments described herein.

Several definitions that apply throughout this disclosure will now be presented.

The connection can be such that the objects are permanently connected or releasably connected. The term "substantially" is defined to be essentially conforming to the particular dimension, shape, or other feature that the term modifies, such that the component need not be exact. The term "comprising" means "including, but not necessarily limited to"; it specifically indicates open-ended inclusion or membership in a so-described combination, group, series, and the like. It should be noted that references to "an" or "one" embodiment in this disclosure are not necessarily to the same embodiment, and such references mean "at least one."

Figure 2:
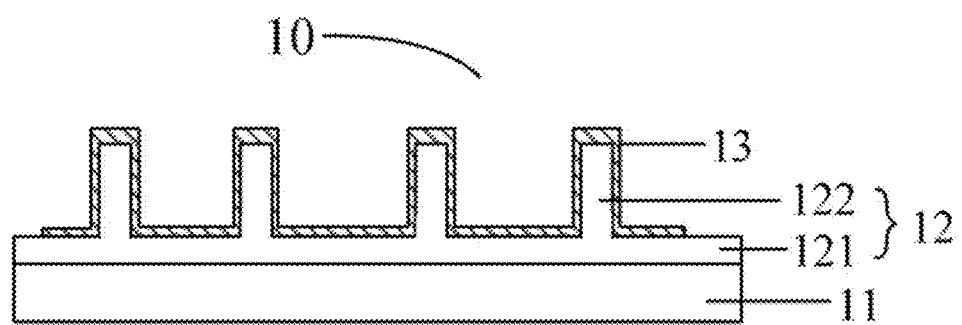
FIG. 2 is a cross-sectional view, along a line II-II of FIG. 1.

FIG. 1 and FIG. 2 show a carrier 10 for use in single molecule of an embodiment detection is provided. The carrier 10 comprises a substrate 11, a middle layer 12 and a metal layer 13. The middle layer 12 is on the substrate 11 surface, and the metal layer 13 is on the middle layer 12 surface. The middle layer 12 comprises a base 121 and a patterned bulge 122 on a surface of the base 121 away from the substrate 11. The patterned bulge 122 comprises a plurality of strip-shaped bulges 125 intersecting with each other to form a net and defines a plurality of holes 124. In one embodiment, the plurality of strip-shaped bulges 125 is an integrated structure.

The substrate 11 can be an insulating substrate or a semiconductor substrate. The substrate 11 is a flexible substrate. The substrate 11 can be placed on a curved surface to be coincident with the curved surface. The substrate 11 can be made of a material such as polyethylene terephthalate (PET), polyimide (PI), polymethylmethacrylate (PMMA), polydimethylsiloxane (PDMS), or polyethylene naphthalate (PEN). The shape, size and thickness of the substrate 11 can be selected according to need. Since the substrate 11 of the carrier 10 is the flexible substrate and can fit on irregular surfaces, the carrier 10 can be used on irregular surfaces for molecular detection in situ. In one embodiment, the material of the substrate 11 is PET, and the substrate 11 is a flat plate.

The base 121 is on a surface of substrate 11. The base 121 defines two surfaces, and the two surfaces are opposite. The patterned bulge 122 can be placed on a single surface or the two surfaces opposite to each other of the base 121. The thickness of the base 121 ranges from 50 nanometers to 300 nanometers. In one embodiment, the thickness of the base 121 ranges from 100 nanometers to 200 nanometers. If the base 121 is too thin, for example, less than 100 nanometers, a Raman spectroscopy of analytes can be interfered by the substrate 11 or affected by the substrate 11. If the base 121 is too thick, for example greater than 200 nanometers, the flexibility of the carrier 10 is reduced. The base 121 can be insulating material such as silicon dioxide, or silicon nitride. The base 121 can also comprise semiconductor materials such as gallium nitride, or gallium arsenide. The base 121 and the patterned bulge 122 can have the same material or different materials. In one embodiment, the base 121 and the patterned bulge 122 are integrated structures, the material of the integrated structure is silicon dioxide. The patterned bulge 122 comprises the plurality of strip-shaped bulges 125. The plurality of strip-shaped bulges 125 comprises a plurality of first strip-shaped bulges 126 and a plurality of second strip-shaped bulges 127. The plurality of first strip-shaped bulges 126 are substantially parallel to each other and extends along a first direction, and the plurality of second strip-shaped bulges 127 are substantially parallel to each other and extend along a second direction, which is different from the first direction. The angle between the first direction and the second direction is greater than 0 degrees and less than or equal to 90 degrees. In one embodiment, the angle between the first direction and the second direction is greater than 30 degrees. In one embodiment, the angle between the first direction and the second direction is 90 degrees. Each of the plurality of strip-shaped bulges 125 has a length less than or equal to the width of length of the base 121.

The width of the plurality of strip-shaped bulges 125 can range from between about 20 nanometers to about 150 nanometers. In one embodiment, the width of the plurality of strip-shaped bulges 125 can be in a range from about 50 nanometers to about 100 nanometers. The height of the plurality of strip-shaped bulges 125 range from about 100 nanometers to 500 nanometers. In one embodiment, the height of the plurality of strip-shaped bulges 125 can range from about 200 nanometers to 400 nanometers. In one embodiment, the height of the plurality of strip-shaped bulges 125 is 300 nanometers. The distance between two adjacent strip-shaped bulges 125 can range from about 10 nanometers to about 300 nanometers. In one embodiment, the distance between two adjacent strip-shaped bulges 125 can range from about 10 nanometers to about 50 nanometers. The average diameter of the plurality of holes 124 can range from about 10 nanometers to about 300 nanometers, and the depth of the plurality of holes 124 can range from about 100 nanometers to about 500 nanometers.

The metal layer 13 is on surfaces of the patterned bulge 122. The metal layer 13 can be a continuous structure. The metal layer 13 can be formed on both top and side surfaces of the plurality of strip-shaped bulges 125 and bottom surfaces of the plurality of holes 124. The metal layer 13 can also be formed as a discontinuous structure. The metal layer 13 can be formed on side surfaces of the plurality of strip-shaped bulges 125 and bottom surfaces of the plurality of holes 124. The metal layer 13 can be formed as a single-layer or a multi-layer structure. At the hole 124 between two adjacent strip-shaped bulges 125, a surface plasmon resonance (SPR) is produced on a surface of the metal layer 13 so that the surface improved Raman scattering (SERS) of the carrier 10 will be outstandingly improved. The thickness of the metal layer 13 can range from about 2 nanometers to about 200 nanometers. The material of the metal layer 13 can be gold, silver, copper, platinum, iron, nickel, aluminum, or any alloy thereof. The metal layer 13 can be uniformly deposited on the surface of the substrate 11 by a method of electron beam evaporation, chemical vapor deposition (CVD), or sputtering. In one embodiment, the metal layer 13 is a gold layer with a thickness of about 10 nanometers.

Figure 3:
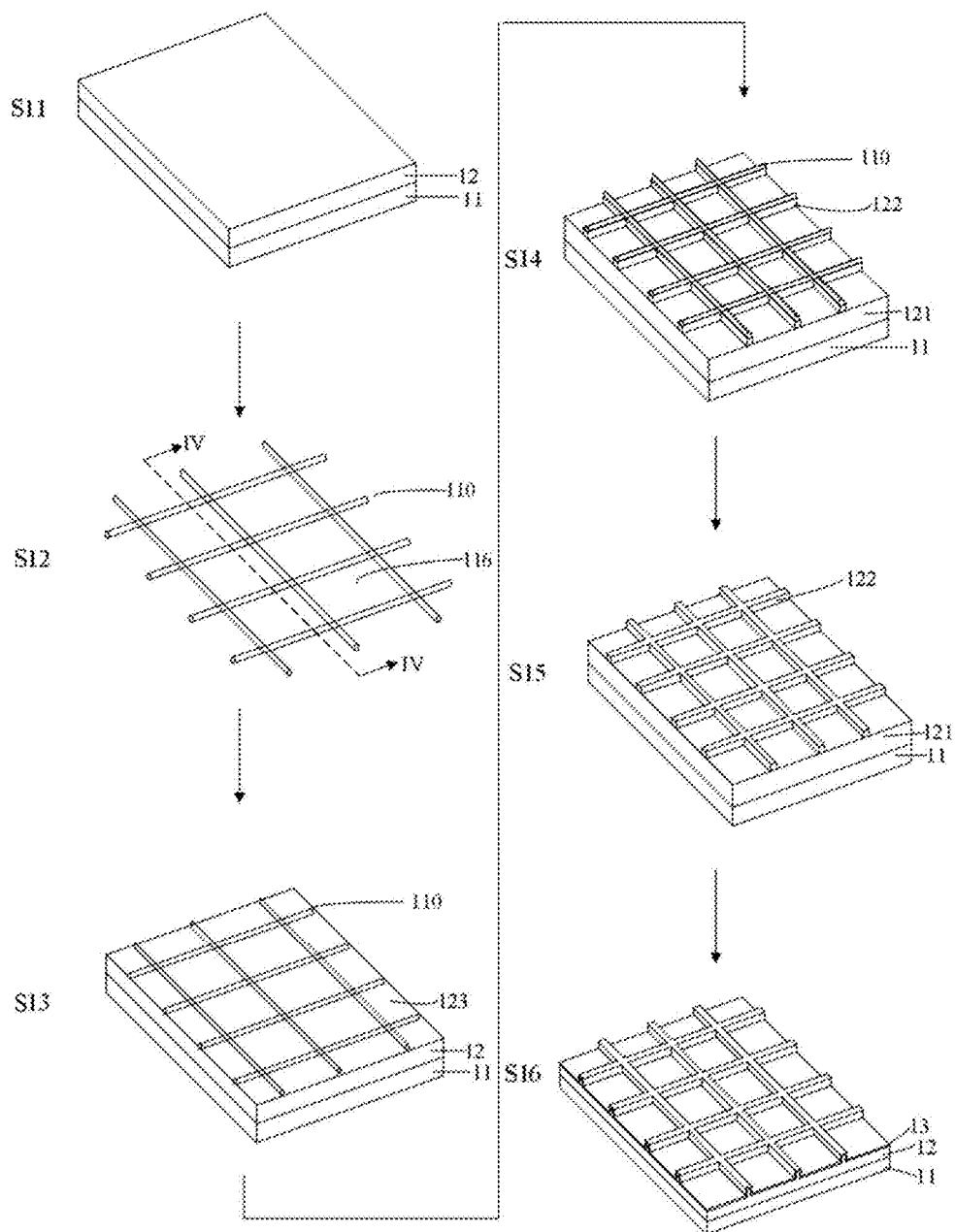
FIG. 3 is a flow chart of a method for making carrier for the single molecule detection.
Figure 4:
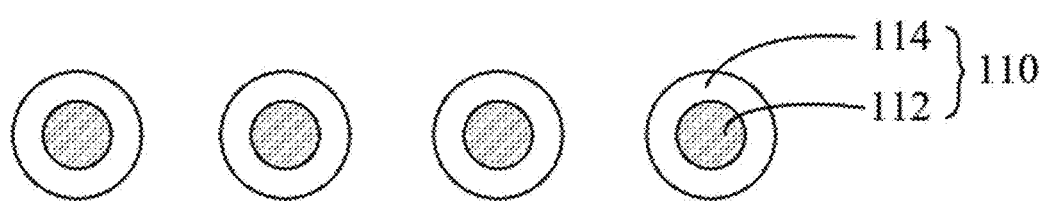
FIG. 4 is a cross-sectional view, along a line IV-IV of FIG. 3.

FIGS. 3-4 show a method for making the carrier 10 of one embodiment. The method includes the following blocks:

block (B11) of placing the middle layer 12 on the substrate 11;

block (B12) of providing a carbon nanotube composite structure 110, wherein the carbon nanotube composite structure 110 includes a plurality of intersected carbon nanotubes and defines a plurality of openings 116;

block (B13) of placing the carbon nanotube composite structure 110 on a surface 123 of the middle layer 12, in which parts of the surface 123 are exposed through the plurality of openings 116;

block (B14) of forming the patterned bulge 122 by dry etching the middle layer 12 using the carbon nanotube composite structure 110 as a mask, in which the patterned bulge 122 includes a plurality of strip-shaped bulges 125 intersected with each other;

block (B15) of removing the carbon nanotube composite structure 110; and block (B16) of depositing the metal layer 13 on the patterned bulge 122 surface.

In block B11, the material of the middle layer 12 can be insulating material or semiconductor material. The insulating material can be silicon dioxide or silicon nitride. The semiconductor material can be silicon, gallium nitride, or gallium arsenide. The middle layer 12 is placed on the substrate 11 surface and in direct contact with the substrate 11 surface. The method of depositing the middle layer 12 on the substrate 11 surface is not limited. In one embodiment, the middle layer 12 is deposited on the substrate 11 surface by plasma chemical vapor deposition.

In block B12, the carbon nanotube composite structure 110 includes a carbon nanotube structure 112 and a protective layer 114 coated on the carbon nanotube structure 112.

The carbon nanotube structure 112 is a free-standing structure. The term "free-standing structure" including the carbon nanotube structure 112 sustaining the weight of itself when it is hoisted by a portion thereof without any significant damage to its structural integrity. Thus, the carbon nanotube structure 112 can be suspended by two spaced supports.

The plurality of carbon nanotubes can be single-walled carbon nanotubes, double-walled carbon nanotubes, or multi-walled carbon nanotubes. The length and diameter of the plurality of carbon nanotubes can be selected according to need. The diameter of the single-walled carbon nanotubes can range from about 0.5 nanometers to about 10 nanometers. The diameter of the double-walled carbon nanotubes can range from about 1.0 nanometer to about 15 nanometers. The diameter of the multi-walled carbon nanotubes can range from about 1.5 nanometers to about 50 nanometers. The length of the carbon nanotubes is greater than 50 micrometers. In one embodiment, the length of the carbon nanotubes can range from about 200 micrometers to about 900 micrometers.

The carbon nanotubes are orderly arranged to form an ordered carbon nanotube structure. The plurality of carbon nanotubes extends along a direction substantially parallel to the surface of the carbon nanotube structure 112. The term 'ordered carbon nanotube structure' includes, but is not limited to, a structure wherein the plurality of carbon nanotubes are arranged approximately along the same direction.

The carbon nanotube structure 112 defines a plurality of apertures. The aperture extends throughout the carbon nanotube structure 112 along a thickness direction thereof. The aperture can be a hole created by several adjacent carbon nanotubes, or a gap created by two substantially parallel carbon nanotubes and extending along an axial direction of the carbon nanotubes. The hole shaped aperture and the gap shaped aperture can exist in the carbon nanotube structure 112 simultaneously. Hereafter, the aperture sizes are referred as the diameter of the hole or width of the gap. The sizes of the apertures can be different. The average aperture sizes can range from about 1 nanometer to about 500 micrometers. For example, the sizes of the apertures can be about 10 nanometers, 50 nanometers, 100 nanometers, 500 nanometers, 1 micrometer, 10 micrometers, 80 micrometers, or 120 micrometers.

The carbon nanotube structure 112 includes at least one carbon nanotube film, at least one carbon nanotube wire, or combination thereof. In one embodiment, the carbon nanotube structure 112 includes a single carbon nanotube film or two or more carbon nanotube films stacked together. The thickness of the carbon nanotube structure 112 can therefore be controlled by the number of the stacked carbon nanotube films. The number of the stacked carbon nanotube films can be in a range from about 2 to about 100. For example, the number of the stacked carbon nanotube films can be 10, 30, or 50. In one embodiment, the carbon nanotube structure 112 is formed by folding a single carbon nanotube wire. In one embodiment, the carbon nanotube structure 112 may include a layer of carbon nanotube wires that are parallel and spaced from each other. Also, the carbon nanotube structure 112 includes a plurality of carbon nanotube wires intersected or weaved together to form a carbon nanotube net. The distance between two adjacent parallel and spaced carbon nanotube wires can range from about 0.1 micrometers to about 200 micrometers. In one embodiment, the distance between two adjacent parallel and spaced carbon nanotube wires is in a range from about 10 micrometers to about 100 micrometers. The gap between two adjacent substantially parallel carbon nanotube wires is defined as the apertures. The size of the apertures can be controlled by controlling the distance between two adjacent parallel and spaced carbon nanotube wires. The length of the gap between two adjacent parallel carbon nanotube wires can be equal to the length of the carbon nanotube wire. Any carbon nanotube structure described herein can be used in all embodiments.

Figure 5:
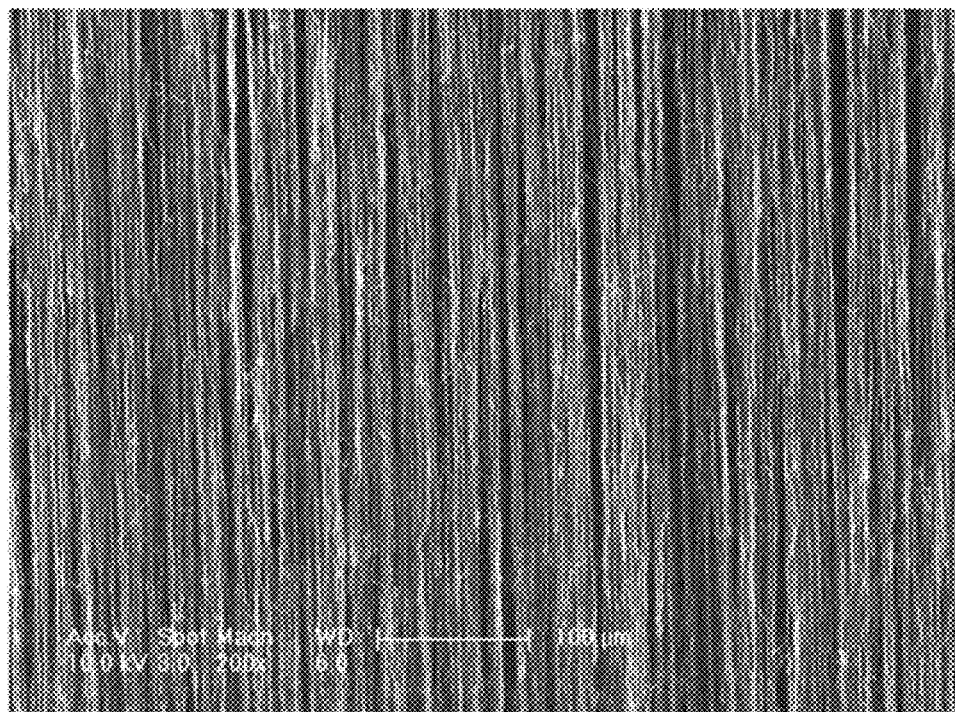
FIG. 5 is a Scanning Electron Microscope (SEM) image of a drawn carbon nanotube film.

In one embodiment, the carbon nanotube structure 112 includes at least one drawn carbon nanotube film. The drawn carbon nanotube film can be drawn from a carbon nanotube array having a drawn film therefrom. The drawn carbon nanotube film includes a plurality of carbon nanotubes joined end-to-end by van der Waals attractive force therebetween. The drawn carbon nanotube film is a free-standing film. Referring to FIG. 5, each drawn carbon nanotube film includes a plurality of successively oriented carbon nanotube segments joined end-to-end by van der Waals attractive force therebetween. Each carbon nanotube segment includes a plurality of carbon nanotubes parallel to each other, and combined by van der Waals attractive force therebetween. As shown in FIG. 5, some variations can occur in the drawn carbon nanotube film. The carbon nanotubes in the drawn carbon nanotube film are oriented along a preferred orientation. The drawn carbon nanotube film can be treated with an organic solvent to increase the mechanical strength and toughness, and reduce the coefficient of friction of the drawn carbon nanotube film. A thickness of the drawn carbon nanotube film can range from about 0.5 nanometers to about 100 micrometers. The drawn carbon nanotube film defines a plurality of apertures between adjacent carbon nanotubes.

In an embodiment, the carbon nanotube structure 112 includes at least two stacked drawn carbon nanotube films. In other embodiments, the carbon nanotube structure 112 includes two or more coplanar carbon nanotube films, and further includes layers of coplanar carbon nanotube films. Additionally, when the carbon nanotubes in the carbon nanotube film are aligned along one preferred orientation (e.g., the drawn carbon nanotube film), the orientations of carbon nanotubes in adjacent films are different, an angle can exist between the orientations of carbon nanotubes in adjacent films, whether stacked or adjacent. Adjacent carbon nanotube films can be combined only by the van der Waals attractive force therebetween. An angle between the carbon nanotubes alignment directions in two adjacent carbon nanotube films can range from about 0 degrees to about 90 degrees. When the angle between the carbon nanotubes alignment directions in adjacent stacked drawn carbon nanotube films is larger than 0 degrees, a plurality of micropores is defined by the carbon nanotube structure 112. In one embodiment, the carbon nanotube structure 112 has the carbon nanotubes alignment directions between adjacent stacked drawn carbon nanotube films at 90 degrees. Stacking the carbon nanotube films will also add to the structural integrity of the carbon nanotube structure 112.

Figure 6:
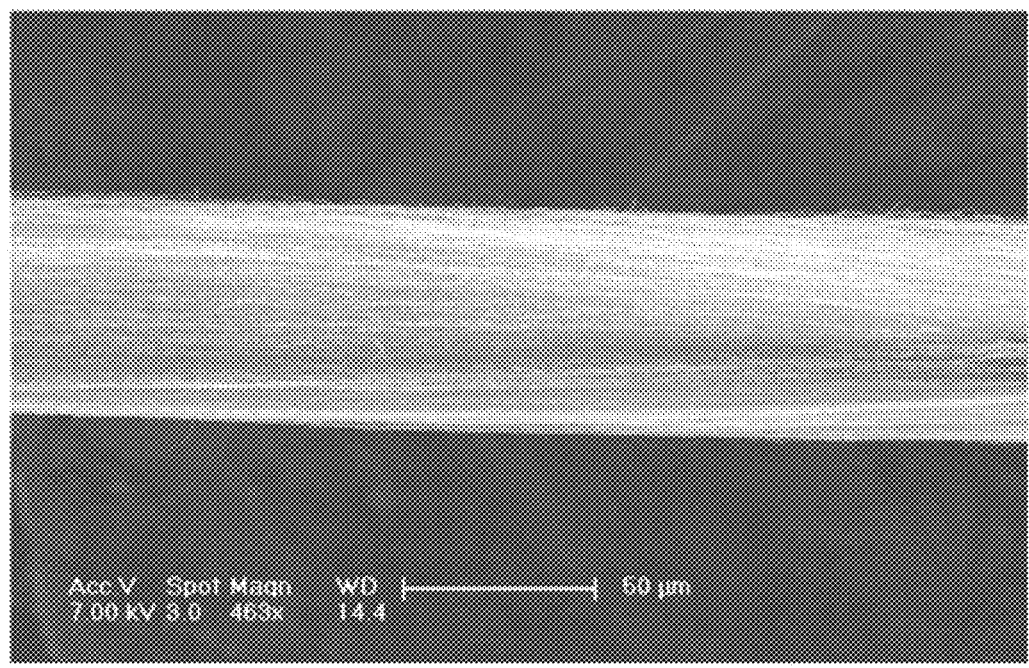
FIG. 6 is an SEM image of an untwisted carbon nanotube wire.

The carbon nanotube wires can be untwisted or twisted. Treating the drawn carbon nanotube film with a volatile organic solvent can form the untwisted carbon nanotube wire. Specifically, the using organic solvent is used to soak the entire surface of the drawn carbon nanotube film. While soaking, adjacent parallel carbon nanotubes in the drawn carbon nanotube film will bundle together, due to the surface tension of the organic solvent as it volatilizes, and thus, the drawn carbon nanotube film will be shrunk into an untwisted carbon nanotube wire. FIG. 6 shows the untwisted carbon nanotube wire includes a plurality of carbon nanotubes substantially oriented along the same direction (i.e., a direction along the length of the untwisted carbon nanotube wire). The carbon nanotubes are substantially parallel to the axis of the untwisted carbon nanotube wire. More specifically, the untwisted carbon nanotube wire includes a plurality of successive carbon nanotube segments joined end to end by van der Waals attractive force therebetween. Each carbon nanotube segment includes a plurality of carbon nanotubes substantially parallel to each other, and combined by van der Waals attractive force therebetween. The carbon nanotube segments can vary in width, thickness, uniformity, and shape. The length of the untwisted carbon nanotube wire can be arbitrarily set as desired. A diameter of the untwisted carbon nanotube wire ranges from about 0.5 nanometers to about 100 micrometers.

Figure 7:
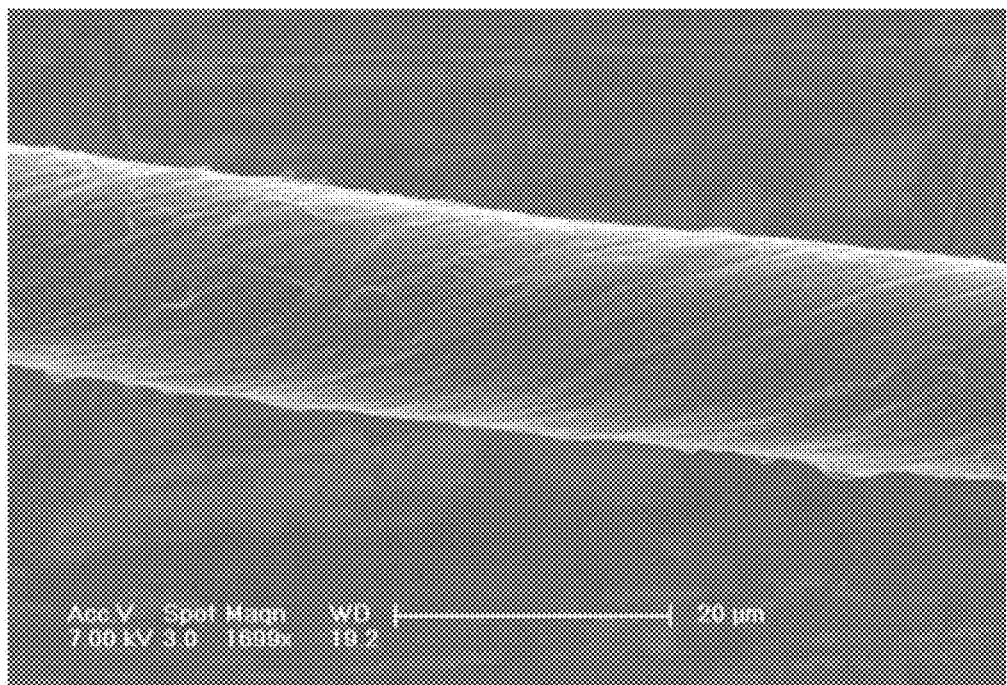
FIG. 7 is an SEM image of a twisted carbon nanotube wire.

The twisted carbon nanotube wire can be formed by twisting a drawn carbon nanotube film using a mechanical force to turn the two ends of the drawn carbon nanotube film in opposite directions. FIG. 7 shows the twisted carbon nanotube wire including a plurality of carbon nanotubes helically oriented around an axial direction of the twisted carbon nanotube wire. More specifically, the twisted carbon nanotube wire includes a plurality of successive carbon nanotube segments joined end to end by van der Waals attractive force therebetween. Each carbon nanotube segment includes a plurality of carbon nanotubes that are parallel with each other, and combined by van der Waals attractive force therebetween. The length of the carbon nanotube wire can be set as desired. A diameter of the twisted carbon nanotube wire can be from about 0.5 nanometers to about 100 micrometers. Further, the twisted carbon nanotube wire can be treated with a volatile organic solvents bundle the adjacent paralleled carbon nanotubes together. By treating the twisted carbon nanotube wire with the volatile organic solvent, the specific surface area of the twisted carbon nanotube wire will decrease, while the density and strength of the twisted carbon nanotube wire will increase.

The carbon nanotube composite structure 110 can be made by applying a protective layer 114 on a surface of the carbon nanotube structure 112. The carbon nanotube structure 112 can be suspended in a depositing chamber during depositing the protective layer 114 so that two opposite surfaces of the carbon nanotube structure 112 are coated with the protective layer 114. In some embodiments, each of the plurality of carbon nanotubes is fully enclosed by the protective layer 114. In one embodiment, the carbon nanotube structure 112 is on a frame so that the middle portion of the carbon nanotube structure 112 is suspended through the through hole of the frame. The frame can be any shape, such as a quadrilateral. The carbon nanotube structure 112 can also be suspended by a metal mesh or metal ring.

The method of depositing the protective layer 114 can be physical vapor deposition (PVD), chemical vapor deposition (CVD), atomic layer deposition (ALD), magnetron sputtering, or spraying.

The plurality of openings 116 are formed by depositing the protective layer 114 on the carbon nanotube structure 112 with the plurality of apertures. The plurality of openings 116 and the plurality of apertures have the same shape having different size. The size of the plurality of openings 116 is smaller than that of the plurality of apertures because the protective layer 114 is deposited in the plurality of apertures.

The thickness of the protective layer 114 is in a range from about 3 nanometers to about 50 nanometers. In one embodiment, the thickness of the protective layer 114 is in a range from about 3 nanometers to about 20 nanometers. If the thickness of the protective layer 114 is less than 3 nanometers, the protective layer 114 cannot prevent the carbon nanotubes from being destroyed following an etching process. If the thickness of the protective layer 114 is greater than 50 nanometers, the plurality of apertures may be fully filled by the protective layer 114 and the plurality of openings 116 may not be formed.

The material of the protective layer 114 can be metal, metal oxide, metal nitride, metal carbide, metal sulfide, silicon oxide, silicon nitride, or silicon carbide. The metal can be gold, nickel, titanium, iron, aluminum, titanium, chromium, or alloy thereof. The metal oxide can be alumina, magnesium oxide, zinc oxide, or hafnium oxide. The material of the protective layer 114 is not limited above and can be any material as long as the material can be deposited on the carbon nanotube structure 112, would not react with the carbon nanotubes and would not be etched easily following a drying etching process. The protective layer 114 is combined with the carbon nanotube structure 112 by van der Waals attractive force therebetween only.

Figure 8:
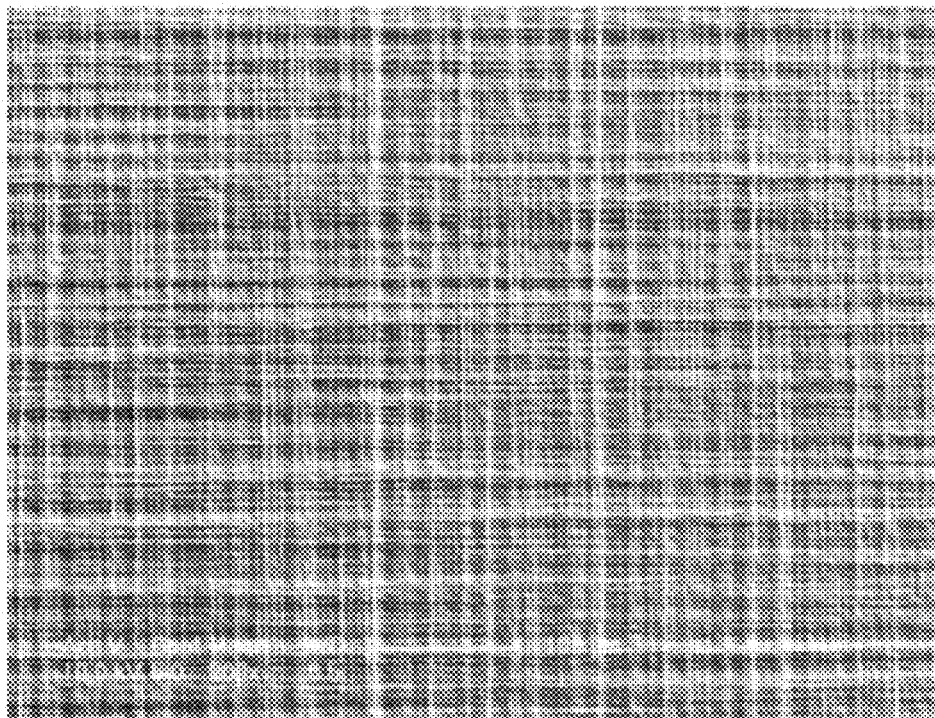
FIG. 8 is an SEM image of a carbon nanotube composite structure.
Figure 9:
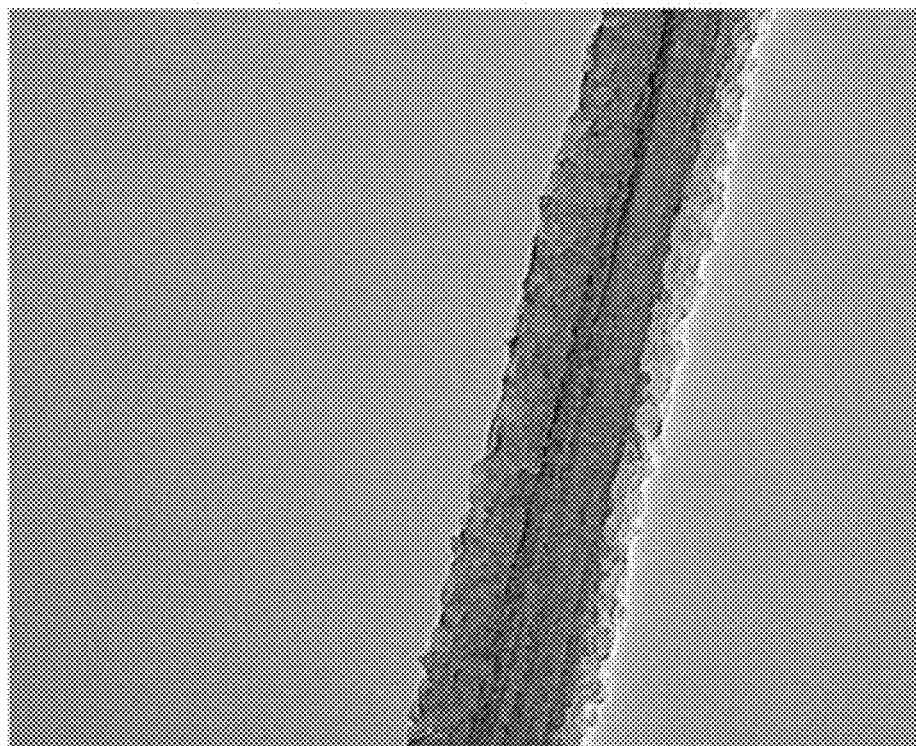
FIG. 9 is an SEM image of a single carbon nanotube coated with an alumina ($Al_2O_3$) layer.

FIG. 8 shows, an alumina layer of 5 nanometers thickness being deposited on two stacked drawn carbon nanotube films by electron beam evaporation in one embodiment. FIG. 9 shows each of the carbon nanotubes being entirely coated by the alumina layer. The carbon nanotubes alignment directions between adjacent stacked drawn carbon nanotube films is 90 degrees.

In block B13, the carbon nanotube composite structure 110 can be in direct contact with the surface 123 of the middle layer 12 or being suspended above the surface 123 of the middle layer 12 by a support. In one embodiment, the carbon nanotube composite structure 110 is transferred on the surface 123 of the middle layer 12 through the frame.

In one embodiment, the block of placing the carbon nanotube composite structure 110 on the surface 123 further comprises solvent treating the middle layer 12 with the carbon nanotube composite structure 110 thereon. Because there is air between the carbon nanotube composite structure 110 and the surface 123 of the middle layer 12, the treating solvent can exhaust the air and allow the carbon nanotube composite structure 110 to be adhered on the surface 123 of the middle layer 12 closely and firmly. The treating solvent can be applied to entire surface of the carbon nanotube composite structure 110 or used to immerse the entire middle layer 12 with the carbon nanotube composite structure 110. The solvent can be water or volatile organic solvent such as ethanol, methanol, acetone, dichloroethane, chloroform, or mixtures thereof. In one embodiment, the organic solvent is ethanol.

In block B14, the dry etching includes plasma etching or reactive ion etching (RIE). In one embodiment, the dry etching is performed by applying plasma energy on the entire or part surface of the surface 123 using a plasma device. The plasma gas can be an inert gas and/or etching gases, such as argon (Ar), helium (He), chlorine (Cl2), hydrogen ($H_2$), oxygen ($O_2$), fluorocarbon ($CF_4$), ammonia ($NH_3$), or air.

In one embodiment, the plasma gas is a mixture of chlorine and argon. The power of the plasma device can be in a range from about 20 watts to about 70 watts. The plasma flow of chlorine can be in a range from about 5 sccm to about 20 sccm, such as 10 sccm. The plasma flow of argon can be in a range from about 15 sccm to about 40 sccm, such as 25 sccm. When the plasma is produced in a vacuum, the work pressure of the plasma can be in a range from about 3 Pa to 10 Pa, such as 6 Pa. The time for plasma etching can be in a range from about 10 seconds to about 20 seconds. The plasma etching time can be, for example, 15 seconds.

During plasma etching process, while the plasma gas reacts with the exposed portion of the middle layer 12, the plasma gas does not react with the protective layer 114. Even if the reaction between the plasma gas and the protective layer 114 to occur, the reaction would be much slower than reaction between the plasma gas and the middle layer 12. The relationship of selecting the plasma gas, material of the middle layer 12 and material of the protective layer 114 is shown in Table 1 below.

TABLE 1

| number | middle layer | protective layer | plasma gas |
|---|---|---|---|
| 1 | $SiO_2$ | Al, Cr, Fe, Ti, Ni, or Au | $CF_4$ |
| 2 | $SiN_x$ | Al, Cr, Fe, Ti, Ni, or Au | $CF_4$ |
| 3 | GaN | $Al_2O_3$ | $Cl_2$, $Ar_2$ |

In the etching process, while the etching gas reacts with the middle layer 12, the etching gas does not react with the protective layer 114. Even if the etching gas to react with the protective layer 114, the reaction speed would be much less than that of the reaction speed between the etching gas and the middle layer 12. Thus, the exposed portion of the middle layer 12 would be etched gradually and the portion of the middle layer 12 that are shielded by the carbon nanotube composite structure 110 would not be etched.

The patterned bulge 122 and the carbon nanotube composite structure 110 substantially have the same pattern. When the carbon nanotube structure 112 includes a plurality of intersecting drawn carbon nanotube films, the patterned bulge 122 includes a plurality of strip-shaped bulges 125 that intersect with each other to form a net structure.

The plurality of strip-shaped bulges 125 can have width ranging from about 20 nanometers to about 150 nanometers, a distance ranging from about 10 nanometers to about 300 nanometers, and a height ranging from about 50 nanometers to about 1000 nanometers.

After coating the carbon nanotubes with the protective layer 114, the diameter of the carbon nanotubes becomes about tens of nanometers, and distance between adjacent two carbon nanotubes becomes about tens of nanometers. Thus, the width and distance of the plurality of strip-shaped bulges 125 becomes tens of nanometers, and the average diameter of the plurality of holes 124 is also tens of nanometers. The density of the strip-shaped bulges 125 and the holes 124 would be increased. For example, when both the width and distance of the plurality of strip-shaped bulges 125 are 20 nanometers, the quantity of the strip-shaped bulges 125 and the hole 124 would be 50 within 1 micrometer. Conventional photolithography methods cannot make all the strip-shaped bulges in nano-scale and obtain this density due to the resolution limitation. A surface plasmon resonance (SPR) is produced on a surface of the metal layer 14 where two adjacent plurality of strip shaped bulges 125 forms a gap, causing the surface-enhanced Raman scattering (SERS) of the carrier 10 to be outstandingly enhanced. The enhancement factor of SERS of the carrier 10 can be in a range from about $10^5$ to about $10^{15}$. In one embodiment, the enhancement factor of SERS of the carrier 10 is about $10^{10}$.

In block B15, the method of removing the carbon nanotube composite structure 110 can be ultrasonic method, adhesive tape peeling, or oxidation. In one embodiment, the middle layer 12 with the carbon nanotube composite structure 110 thereon is placed in an N-methylpyrrolidone solution and ultrasonic treating for several minutes.

In block B16, the metal layer 13 can be deposited on the patterned bulge 122 by a method of electron beam evaporation, ion beam sputtering, atomic layer deposition, magnetron sputtering, thermal vapor deposition, or chemical vapor deposition. The thickness of the metal layer 13 can be in a range from about 2 nanometers to about 200 nanometers. The material of the metal layer 14 can be gold, silver, copper, iron, nickel, aluminum or alloy of any combination thereof. In one embodiment, the metal layer 14 is a gold layer with a thickness of about 10 nanometers.

Figure 10:
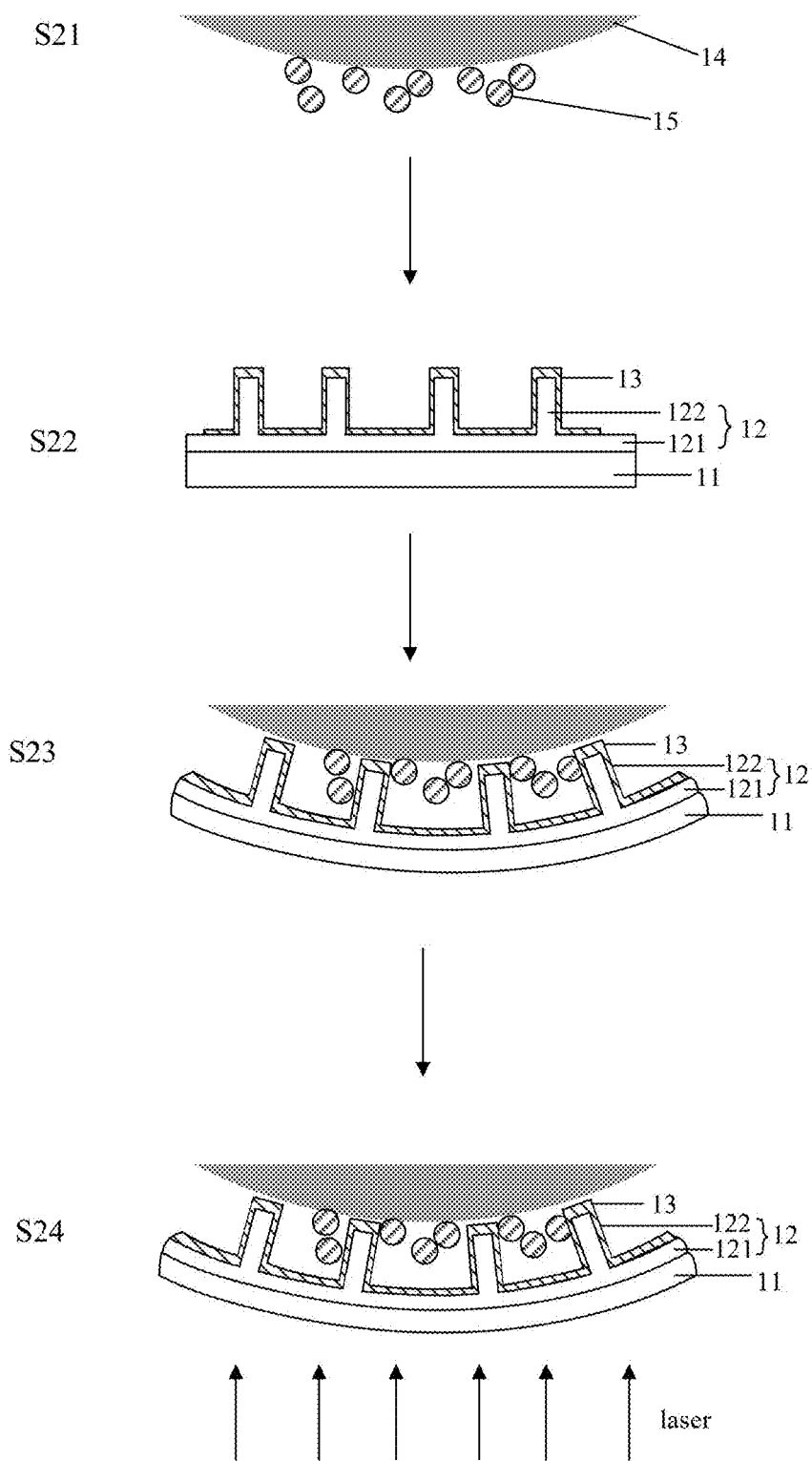
FIG. 10 is a flow chart of a method for detecting single molecules.

FIG. 10 shows a method for detecting single molecule of one embodiment in which the method includes the following blocks:

block (B21) of providing a sample 14 to be tested, in which a surface of the sample 14 is distributed with analyte molecules 15;

block (B22) of providing the carrier 10, in which the carrier 10 comprising a substrate 11, a middle layer 12 and a metal layer 13, the middle layer 12 is sandwiched between the substrate 11 and the metal layer 13, the middle layer 12 comprises a base 121 and a patterned bulge 122 on a surface of the base 120, the patterned bulge 122 comprises a plurality of strip-shaped bulges 125 intersected with each other to form a net and define a number of holes 124, and the metal layer 13 is on the patterned bulge 122;

block (B23) of placing the carrier 10 on the surface of the sample 14, in which the metal layer 13 is attached to the surface of the sample 14 so that the analyte molecules 15 are formed on the metal layer 13; and block (B24) of detecting the analyte molecules 15 on the metal layer 13 with a detector.

In block B21, the surface of the sample 14 can be any surface such as a plane, a curved surface or other irregular surface. The sample 14 can be a fruit or vegetable, such as an apple or a tomato. The type of the analyte molecules 15 is not limited, and the analyte molecules 15 can be arbitrarily distributed on the surface of the sample 14 to be tested. For example, the analyte molecules 15 can be pesticides remaining on the surface of the tomato. In one embodiment, the analyte molecules 15 is CV molecules.

In block B23, the carrier 10 is attached to the surface of the sample 14, the curvature of the carrier 10 is consistent with the curvature of the surface of the sample 14. The metal layer 13 is in direct contact with the surface of the sample 14. Thus, the analyte molecules 15 can be adhered to the metal layer 13. Before the metal layer 13 is attached to the surface of the sample 14, appropriate amount of solvent can be applied on the surface of the sample 14 to dissolve the analyte molecules 15. Since the fluidity of the analyte molecules 15 is improved by the method, the analyte molecules 15 easily adhere to the surface of the metal layer 13. Because of air between the surface of the sample 14 and the metal layer 13, the solvent can exhaust the air and allow the carrier 10 to adhere on the surface of the sample 14 closely and firmly. The solvent can be water, ethanol, or propanol. The area on which the solvent is spread on the surface of the sample 14 is equal to or slightly larger than the area of the metal layer 13.

Figure 11:
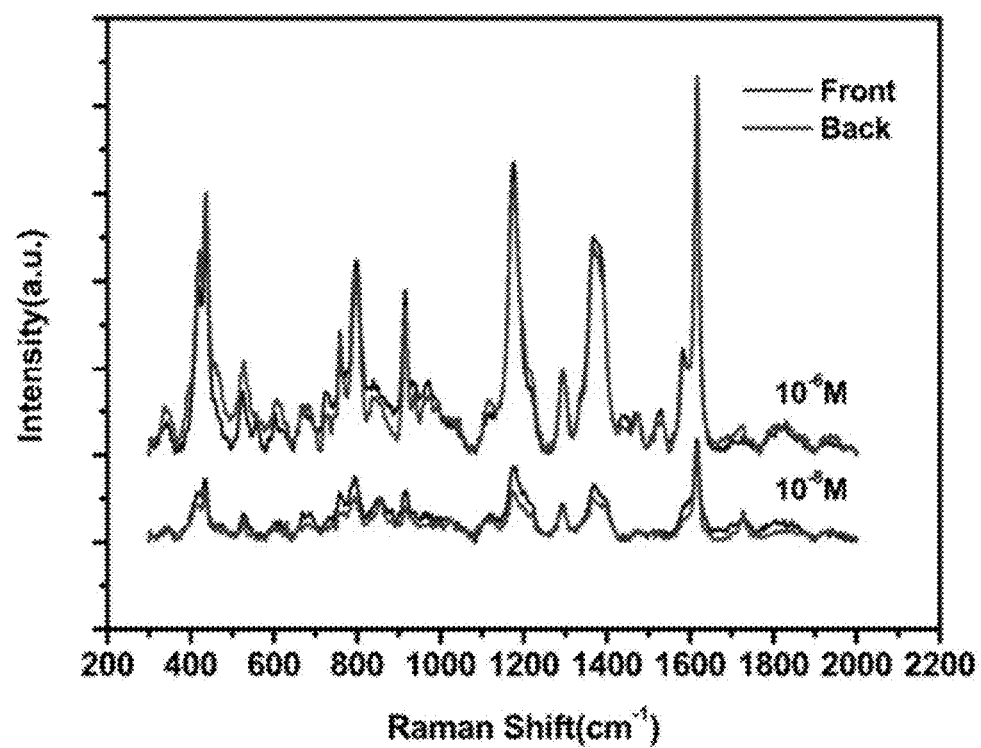
FIG. 11 is a Raman spectroscopy of analytes with different concentrations measured from both sides of the carrier.

In block B24, the detector such as Raman spectrometer can directly detect the analyte molecule 15 on the surface of the metal layer 13 in situ. It is unnecessary to remove the carrier 10 from the surface of the sample 14. The surface of the metal layer 13 away from the substrate 11 will be the front surface of the carrier 10, and the surface of the substrate 11 away from the metal layer 13 will be the back surface of the carrier 10. The detector can detect the analyte molecule 15 by irradiating laser to the front surface of the carrier 10, the detector can also detect the analyte molecule 15 by irradiating laser to the back surface of the carrier 10. FIG. 11 shows a first Raman spectroscopy detected from the front surface of the carrier 10 being consistent with a second Raman spectroscopy detected from the back surface of the carrier 10.

Figure 12:
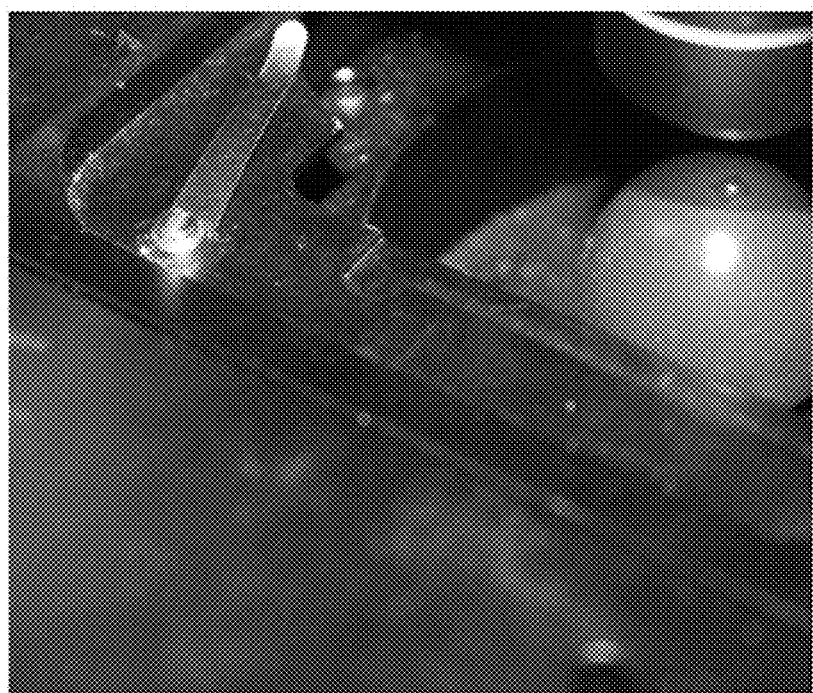
FIG. 12 is a photo of detecting crystal violet (CV) molecules on a tomato's surface by Raman spectrometer in situ.
Figure 13:
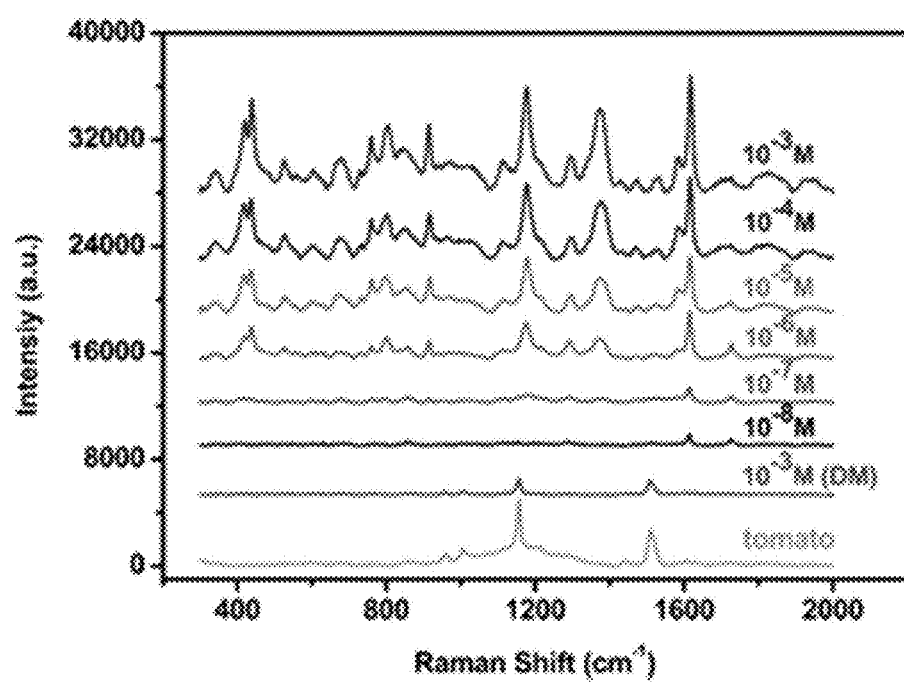
FIG. 13 is a Raman spectroscopy of CV molecules on a tomato's surface.

The analyte molecule 15 can be detected by irradiating laser to the back surface of the carrier 10. FIG. 12 shows a photo of detecting CV molecules on a tomato's surface by Raman spectrometer in situ. FIG. 13 shows the Raman spectroscopy of CV molecules detection on a tomato's surface. In one embodiment, an excitation wavelength of the Raman spectrometer is 633 nanometers, an excitation time of the Raman spectrometer is 5 seconds, and the device power of the Raman spectrometer is 0.1 mW.

Figure 14:
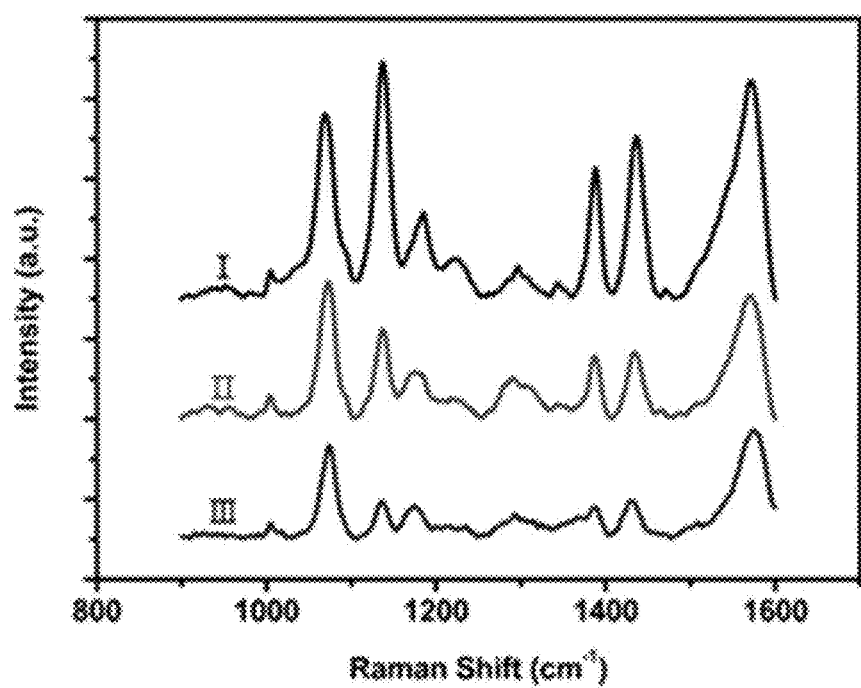
FIG. 14 is a Raman spectroscopy of 4-ATP molecule on the carrier after wiping the surface of apples with the carrier.

The analyte molecule 15 can be detected by irradiating the front surface of the carrier 10. After the metal layer 13 is attached to the surface of the sample 14, the surface of the sample 14 can be wiped by the carrier 10. Thus, part of the analyte molecules 15 can be transferred to the surface of the metal layer 13. Then the carrier 10 including parts of the analyte molecules 15 to be removed from the surface of the sample 14. FIG. 14 shows a comparison chart of a Raman spectroscopy of 4-ATP molecule detected after wiping and detected in situ. In one embodiment, an excitation wavelength of the Raman spectrometer is 633 nanometers, an excitation time of the Raman spectrometer is 5 seconds, and a device power of the Raman spectrometer is 0.1 mW. The Raman spectroscopy of 4-ATP molecule detected after wiping is consistent with the Raman spectroscopy of 4-ATP molecule detected in situ.

Figure 15:
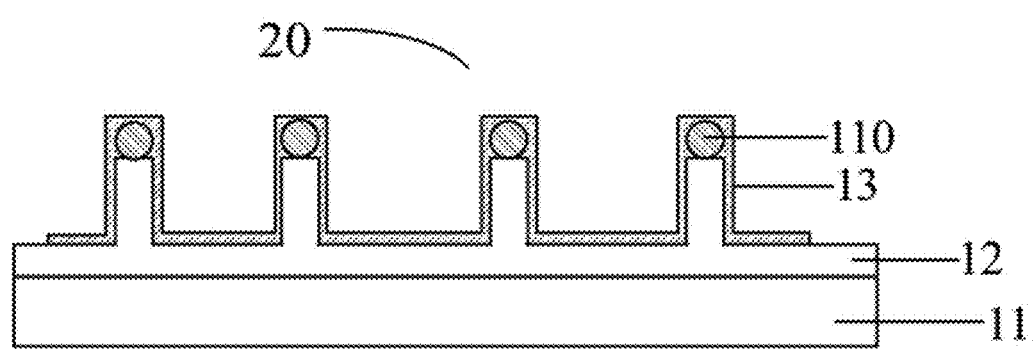
FIG. 15 is a schematic view of a carrier for use in single molecule detection.

FIG. 15 shows a carrier 20 used in single molecule detection of another embodiment. The carrier 20 comprises a substrate 11, a middle layer 12 and a metal layer 13. The middle layer 12 is on the substrate 11 surface, and the metal layer 13 is on the middle layer 12. The middle layer 12 comprises a base 121 and a patterned bulge 122 on a surface of the base 121 away from the substrate 11. The patterned bulge 122 comprises a plurality of strip-shaped bulges 125 intersecting with each other to form a net and defines a plurality of holes 124. In one embodiment, the plurality of strip-shaped bulges 125 is an integrated structure.

The carrier 20 is similar to the carrier 10 above except that the carrier 20 further comprises a carbon nanotube composite structure 110 between the patterned bulge 122 and the metal layer 13. The metal layer 13 entirely covers both the patterned bulge 122 and the carbon nanotube composite structure 110. The carbon nanotube composite structure 110 is on the top surface of the plurality of strip-shaped bulges 125.

Figure 16:
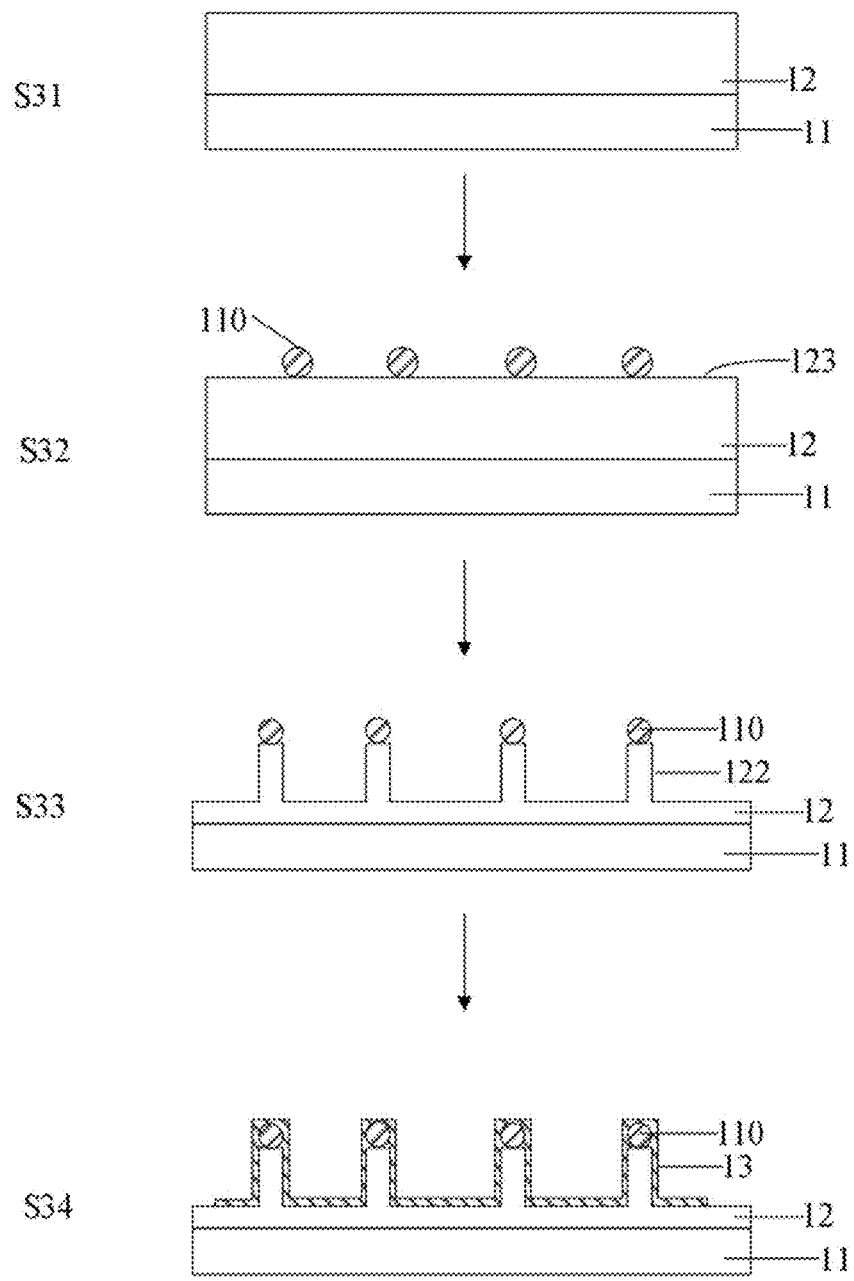
FIG. 16 is a flow chart of a method for making carrier for the single molecule detection.

FIG. 16 shows a method for making the carrier 20 of one embodiment. The method includes the following blocks:

block (S31) of placing the middle layer 12 on the substrate 11;

block (S32) of placing a carbon nanotube composite structure 110 on a surface 123 of the middle layer 12, in which parts of the surface 123 are exposed;

block (S33) of forming the patterned bulge 122 by dry etching the middle layer 12 using the carbon nanotube composite structure 110 as a mask, in which the patterned bulge 122 includes a plurality of strip-shaped bulges 125 intersected with each other; and block (S34) of depositing the metal layer 13 on the patterned bulge 122 surface to cover both the patterned bulge 122 and the carbon nanotube composite structure 110.

The method for making the carrier 20 is similar to the method for making the carrier 10 previously described except that the block of removing the carbon nanotube composite structure 110, therefore is omitted. The metal layer 13 entirely covers both the patterned bulge 122 and the carbon nanotube composite structure 110.

The carbon nanotube composite structure 110 and the patterned bulge 122 can form two layers of nano-scaled structure, in which the carbon nanotube composite structure 110 and the patterned bulge 12 having the same pattern. The carbon nanotube composite structure 110 can increase the roughness of the top surfaces of the patterned bulge 122. Thus, the SERS of the carrier 20 is further improved. Furthermore, the described method for making the carrier 20 would have a relatively lower cost and relatively higher efficiency to conventional methods, and cause less pollution because the block of removing the carbon nanotube composite structure 110, however, the method is omitted.

Figure 17:
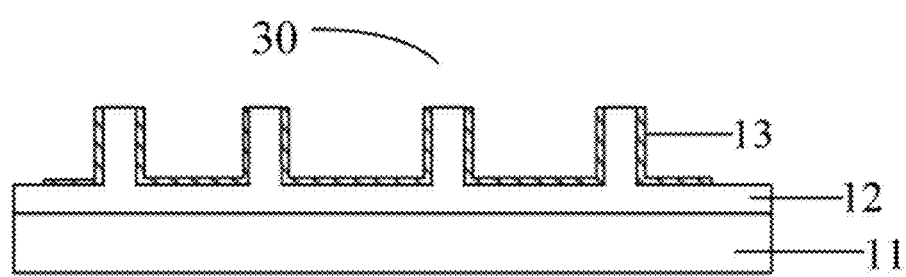
FIG. 17 is a schematic view of a carrier for use in single molecule detection.

FIG. 17 shows a carrier 30 used in single molecule detection of another embodiment. The carrier 30 comprises a substrate 11, a middle layer 12 and a metal layer 13. The middle layer 12 is on the substrate 11 surface, and the metal layer 13 is on the middle layer 12. The middle layer 12 comprises a base 121 and a patterned bulge 122 on a surface of the base 121 away from the substrate 11. The patterned bulge 122 comprises a plurality of strip-shaped bulges 125 intersecting with each other to form a net and forms a plurality of holes 124. In one embodiment, the plurality of strip-shaped bulges 125 form an integrated structure.

The carrier 30 is similar to the carrier 10 previously described, except that the metal layer 13 is discontinuous. The metal layer 13 is only on side surfaces of the plurality of strip-shaped bulges 125 and bottom surfaces of the plurality of holes 124. The top surfaces of the plurality of strip-shaped bulges 125 are free of any metal layer. Alternatively, the metal layer 14 can be only on bottom surfaces of the plurality of holes 124, and the top and side surfaces of the plurality of strip-shaped bulges 125 are free of any metal layer.

Figure 18:
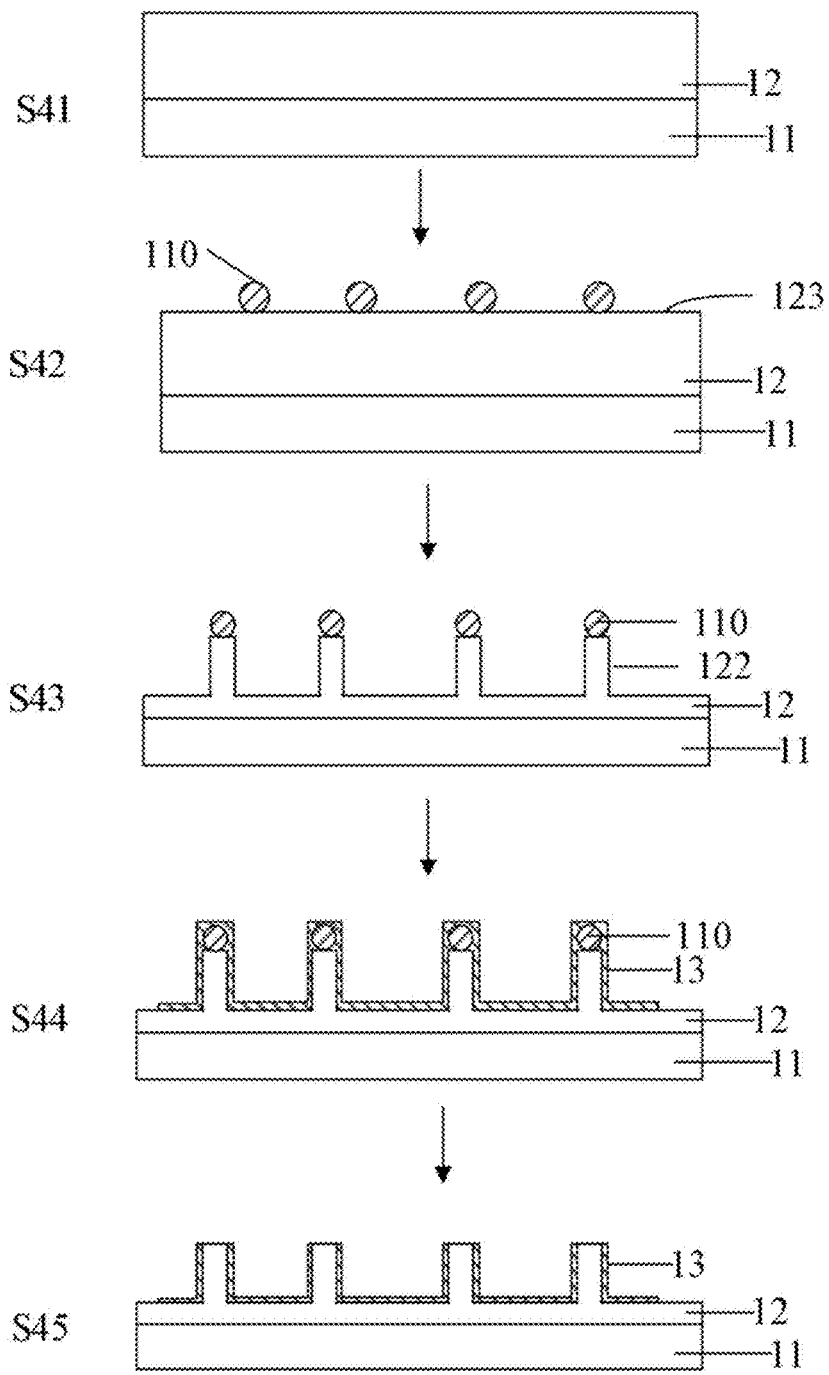
FIG. 18 is a flow chart of a method for making carrier for the single molecule detection.

FIG. 18 shows a method for making the carrier 30 of one embodiment. The method includes the following blocks:

block (B41) of placing the middle layer 12 on the substrate 11;

block (B42) of placing a carbon nanotube composite structure 110 on a surface 123 of the middle layer 12, in which parts of the surface 123 are exposed;

block (B43) of forming the patterned bulge 122 by dry etching the middle layer 12 using the carbon nanotube composite structure 110 as a mask, in which the patterned bulge 122 includes a plurality of strip-shaped bulges 125 intersected with each other;

block (B44) of depositing the metal layer 13 on the patterned bulge 122 surface to cover both the patterned bulge 122 and the carbon nanotube composite structure 110; and block (B45) of removing the carbon nanotube composite structure 110.

The method for making the carrier 30 is similar to the method for making the carrier 20 previously described, except the carbon nanotube composite structure 110 being removed after applying the metal layer 13 on the patterned bulge 122. In block (B44), a first part of the metal layer 13 is on the surface of the carbon nanotube composite structure 110, and a second part of the metal layer 13 is on the side surfaces of the patterned bulge 122 and the bottom surfaces of the plurality of holes 124. In block (B45), the first part of the metal layer 13 is removed together with the carbon nanotube composite structure 110. Thus, a discontinuous metal layer 13 is obtained. The carbon nanotube composite structure 110 is used as a mask for both etching the surface 121 and depositing the metal layer 13. The cost is relatively lower and the efficiency is relatively higher compared to conventional methods. In the actual preparation process, after removing the carbon nanotube composite structure 110, some metal particles can remain at the boundary between the top surfaces and the side surfaces of the patterned bulge 122. The metal particles remained at the boundary can also be enhancing the SERS of the carrier 30. In one embodiment, the carrier 30 is also used to detect single molecule.

Figure 19:
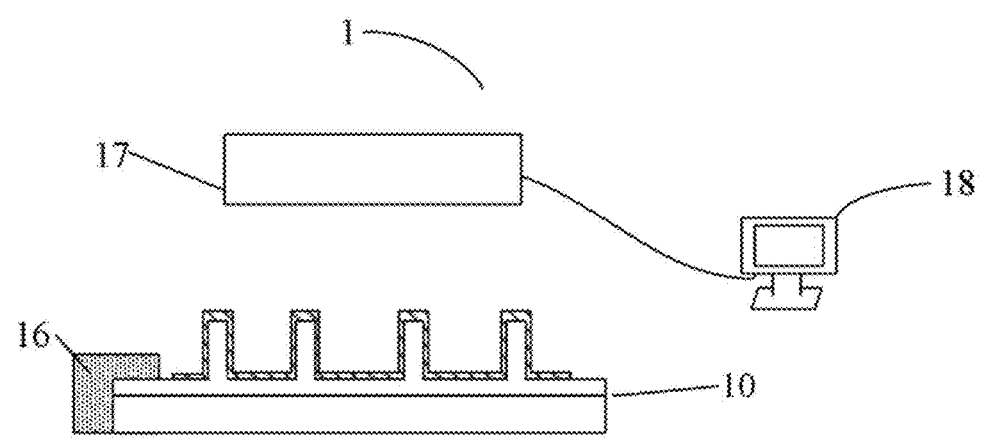
FIG. 19 is a schematic view of a molecular detection device.

FIG. 19 shows a device 1 used in single molecule detection of one embodiment. The device 1 comprises a carrier 10, a fixed element 16 for fixing the carrier 10 on the surface of the sample 14, a detector 17 for detecting molecules on the surface of the carrier 10, and a control computer 18 connected to the detector 17.

Figure 20:
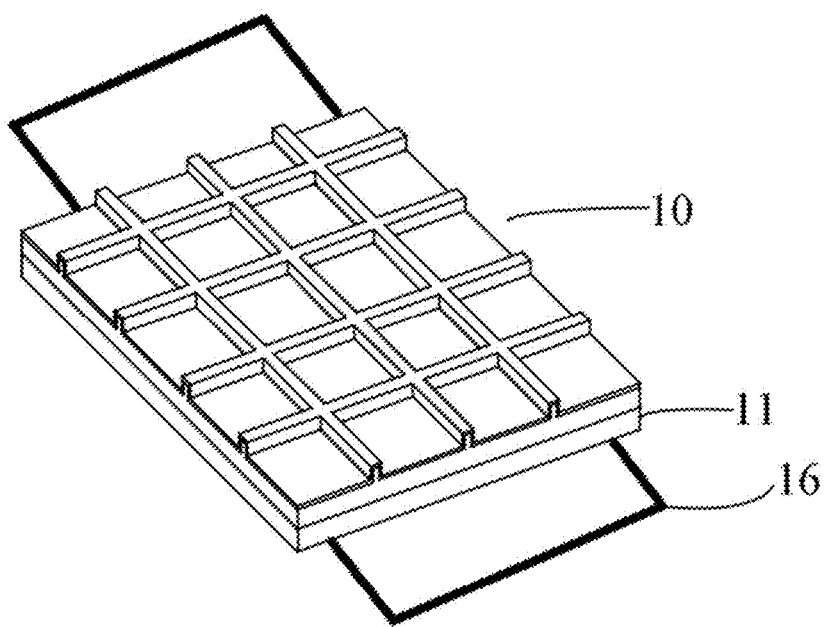
FIG. 20 is a schematic view of a carrier supported by a metal frame.

The fixed element 16 is not limited to any particular shape or size and can be any elements in which the fixed element 16 can fix the carrier 10 on the sample. In one embodiment, the fixed element 16 is a fixing tape. The carrier 10 can be attached to the surface of the sample by the fixing tape. FIG. 20 shows the fixed element 16 being a bendable metal frame, and that edges of the substrate 11 are fixed to the bendable metal frame so that the bendable metal frame can be bent simultaneously with the carrier 10. Furthermore, when the carrier 10 is attached to the surface of the sample 14 alone, the fixed element 16 becomes unessential element. The detector 17 can be a Raman spectrometer or other detector used for molecular detection.

Figure 21:
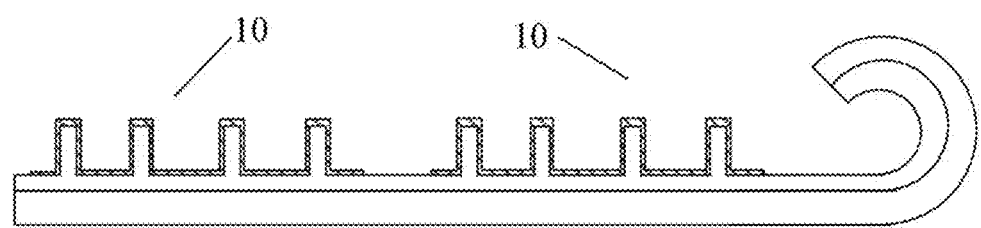
FIG. 21 is a schematic view of a plurality of carriers for use in single molecule detection.

FIG. 21 shows the device 1 further comprising a plurality of carriers 10. The plurality of carriers 10 are connected to form a carrier strip. In one embodiment, the plurality of carriers 10 have a common substrate, and are on the surface of the common substrate. The carrier strip is a flexible structure and can be crimped into a tube to save space. The carrier strip can be taken off as needed during use, thus making the carrier strip easy to use.

In works, the carrier 10 is fixed to the surface of the sample by using the fixed element 16. The detector 17 emits light to detect the analyte molecules 15 on the surface of the carrier 10, obtains a detection result, and sends the detection result to the control computer 18. The control computer 18 receives and analyzes the detection result. Thus, the analyte molecules 15 can be monitored and detected in real-time.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size, and arrangement of the parts within the principles of the present disclosure, up to and including the full extent established by the broad general meaning of the terms used in the claims.

Depending on the embodiment, certain of the blocks of methods described may be removed, others may be added, and the sequence of blocks may be altered. The description and the claims drawn to a method may comprise some indication in reference to certain blocks. However, the indication used is only to be viewed for identification purposes and not as a suggestion for ordering the blocks.

What is claimed is:

1. A carrier for use in single molecule detection, the carrier comprising:
a flexible substrate;
a middle layer, on the flexible substrate;
a metal layer, on the middle layer; and
a carbon nanotube composite structure, between the metal layer and the middle layer;
wherein
the middle layer comprises a base and a patterned bulge on the base,
the patterned bulge comprises a plurality of strip-shaped bulges,
the metal layer is on the patterned bulge, and
the carbon nanotube composite structure is between the metal layer and the patterned bulge.

2. The carrier of claim 1, wherein the flexible substrate comprises a material selected from the group consisting of polyethylene terephthalate, polyimide, polymethylmethacrylate, polydimethylsiloxane, and polyethylene naphthalate.

3. The carrier of claim 1, wherein the thickness of the base ranges from 100 nanometers to 200 nanometers.

4. The carrier of claim 1, wherein the plurality of strip-shaped bulges are intersect with each other to form a net and defines a plurality of holes.

5. The carrier of claim 4, wherein the plurality of strip-shaped bulges comprises a plurality of first strip-shaped bulges and a plurality of second strip-shaped bulges, the plurality of first strip-shaped bulges are substantially parallel with each other and extends along a first direction, and the plurality of second strip-shaped bulges are substantially parallel with each other and extends along a second direction different from the first direction.

6. The carrier of claim 5, wherein an angle between the first direction and the second direction is greater than or equal to 30 degrees and less than or equal to 90 degrees.

7. The carrier of claim 4, wherein each of the plurality of strip-shaped bulges has a width ranging from about 20 nanometers to about 150 nanometers and a height ranging from about 20 nanometers to about 500 nanometers, and a distance between adjacent strip-shaped bulges ranging from about 10 nanometers to about 300 nanometers.

8. The carrier of claim 4, wherein each of the plurality of strip-shaped bulges has a width ranging from about 50 nanometers to about 100 nanometers and a height ranging from about 200 nanometers to about 400 nanometers, and a distance between adjacent strip-shaped bulges is ranging from about 10 nanometers to about 50 nanometers.

9. The carrier of claim 1, wherein the carbon nanotube composite structure is on top surfaces of the patterned bulge.

10. The carrier of claim 1, wherein the thickness of the metal layer ranges from 2 nanometers to 200 nanometers.

11. The carrier of claim 1, wherein the carbon nanotube composite structure comprises a carbon nanotube structure and a protective layer coated on the carbon nanotube structure, and the carbon nanotube structures comprises a plurality of intersecting carbon nanotubes.

12. The carrier of claim 11, wherein the protective layer comprises a material selected from the group consisting of metal, metal oxide, metal nitride, metal carbide, metal sulfide, silicon oxide, silicon nitride, and silicon carbide.

13. The carrier of claim 1, wherein the carbon nanotube structure comprises first carbon nanotube film and a second carbon nanotube film stacked with each other, the first carbon nanotube film comprises a plurality of first carbon nanotubes joined end to end and arranged along a third direction, and the second carbon nanotube film comprises a plurality of second carbon nanotubes joined end to end and arranged along a fourth direction different from the third direction.

14. The carrier of claim 1, wherein the carbon nanotube composite structure and the patterned bulge have the same pattern etched thereon.

15. The carrier of claim 1, further comprises a fixed element, the fixed element is used for fixing the carrier on a surface of a sample.

16. The carrier of claim 15, wherein the fixed element is a fixing tape or a bendable metal frame.

17. The carrier of claim 1, wherein entire carrier is a flexible structure.

* * * * *